(12) United States Patent
Rault

(10) Patent No.: US 6,242,004 B1
(45) Date of Patent: Jun. 5, 2001

(54) BIOADHESIVE TABLETS

(75) Inventor: Isabelle Rault, Mulhouse (FR)

(73) Assignee: Permatec Technologie AG, Zug (CH)

( * ) Notice: Subject to any disclaimer, the term of this patent is extended or adjusted under 35 U.S.C. 154(b) by 0 days.

(21) Appl. No.: 09/063,361

(22) Filed: Apr. 21, 1998

(30) Foreign Application Priority Data

Apr. 23, 1997 (FR) .................................... 97 05028

(51) Int. Cl.$^7$ .................................... A61K 9/24
(52) U.S. Cl. .................... 424/472; 424/434; 424/435; 424/465; 514/772.3
(58) Field of Search .................... 424/464, 465, 424/435, 434, 422, 423, 424, 425, 430, 436, 472

(56) References Cited

U.S. PATENT DOCUMENTS 4,573,996   3/1986   Kwiatek et al. ...................... 604/897
5,849,322   12/1998  Ebert et al. .......................... 424/435

FOREIGN PATENT DOCUMENTS 0 262 422    4/1988   (EP) .
0 649 650    4/1995   (EP) .
2 514 642    4/1983   (FR) .
WO 95/34286  12/1995  (WO) .

*Primary Examiner*—James M. Spear
(74) *Attorney, Agent, or Firm*—Nixon & Vanderhye P.C.

(57) ABSTRACT

The invention relates to bioadhesive compounds in the form of multilayers and having at least one bioadhesive layer with the total charge of bioadhesive material wherein the bioadhesive layer is directly compressible during the production of the tablet, and also containing at least one layer with the total charge of active principals.

23 Claims, 3 Drawing Sheets

Barrier layer

Main layer

Bioadhesive layer

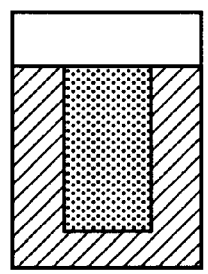
Fig. 1A
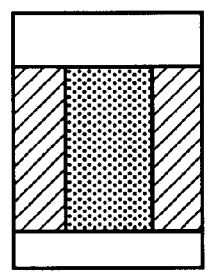
Fig. 1B
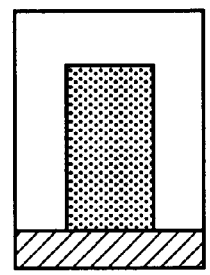
Fig. 1C
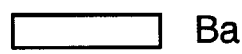 Barrier layer
 Main layer
 Bioadhesive layer ☐ Barrier layer
▒ Main layer
▨ Bioadhesive layer ☐ Barrier layer
▦ Main layer
▨ Bioadhesive layer

BIOADHESIVE TABLETS

The invention relates to tablets having bioadhesive properties, which may be used by the transmucosal route but also, depending on their structure, by the non-transmucosal route.

Transmucosal administration has the advantage, at the metabolic level, of avoiding substantial metabolism of the active principle by the hepatic first-pass effect and hence of reducing the doses administered by improving the clinical efficacy. The active principle does not undergo the various enzymatic or chemical degradation processes along the gastro-intestinal tract, and the disadvantages associated with the function and physiology of the gastrointestinal apparatus.

Numerous formulations have been proposed for improving various properties desired for such tablets, such as bioavailability of the active principle, by controlling its rate of release and the direction of flow of active principle, or the adhesiveness of the tablet on a tissue or a mucous membrane.

In these formulations, the bioadhesive compound is frequently used in mixture with the active principle and other excipients such as swelling agents. The respective properties of these products are not, therefore, fully used to advantage. A part of the bioadhesive compound is in fact trapped in the mixture and is not used for adhesion. Similarly, not all the active principle is always used, and controlling its rate of release may prove difficult.

In other formulations, the choices made for the bioadhesive products make it necessary to use auxiliaries such as gelatin in order to obtain the desired effect.

Generally speaking, the bioadhesive tablets available at present thus have several types of limitations such as insufficient bioadhesion, excessive bulkiness, a structure lacking cohesion in use, or poor control of the intensity and/or the orientation of the flows of active principle(s).

Bioadhesive products are difficult to work industrially because they pose problems of sticking. Due to their hydrophilic nature, they are difficult to process by wet granulation; when processed in a mixture of powders they often exhibit poor flow. Finally, generally speaking, these products are not very suitable for compression.

The inventors have now found that by selecting certain types of bioadhesive compounds and excipients, it was possible to produce a new type of tablets with a succession of layers having distinct functions, and to operate by direct compression in order to produce at least one of these layers.

The object of the invention is, therefore, to provide new optimised tablets in terms of their adhesiveness and diffusion of the active principles that they contain, and hence their efficacy, and which are inexpensive.

In particular, the object is to provide tablets that may be used by the transmucosal or non-transmucosal route, and which may be administered orally if necessary.

The tablets of the invention are characterised in that they take the form of multilayers and that they contain, at least one bioadhesive layer containing the total charge of bioadhesive material, this layer being directly compressible during the production of the tablet, and being capable of adhering to a biological tissue or a mucous membrane by impregnation with water or the biological fluid present in the environment of the tissue or of the mucous membrane, whilst permitting the release of the active principle in the desired manner, and at least one layer containing the majority of the total charge of active principle.

It will be observed that the bioadhesive layer(s) may be compressed directly, which represents a technical advantage compared with the preparation of the bioadhesive tablets available hitherto and allows production at a lower cost.

Moreover, the total charges of active principle and of bioadhesive material are found in distinct layers respectively. Each layer may thus be produced with the minimum quantity of product required for the desired effect. This results in an economic advantage and a benefit for the patient both in medical terms and in terms of his comfort. Thanks to the concentration of the bioadhesive polymer in contact with the tissue or mucous membrane to which the tablet is applied, an intense bioadhesive effect is obtained and a controlled and reproducible release of active principle.

Optimisation of the bioadhesion of the tablets of the invention allows the production of tablets which, compared with those of the prior art, have an increased efficacy and longer period of bioadhesion for an equivalent or lower quantity of bioadhesive compound because it has been optimised. This advantage is particularly beneficial for the administration of active principles over a long period.

According to an advantageous arrangement, the tablet of the invention is characterised in that it contains, moreover, at least one layer forming a barrier to the diffusion of active principle and to the penetration of water or of said biological fluid.

Such a tablet therefore has the advantage not only of orienting the diffusion of the active principle but also of limiting the phenomena of disintegration of the matrix by protecting in particular the tablet from erosion due to the movements of neighbouring tissues (for example, the upper lip in the case of a tablet for buccal administration) by preventing inappropriate sticking of the tablet.

According to an advantageous embodiment, the bioadhesive layer of the tablets of the invention contains, in mixture with the bioadhesive material, at least one swelling agent which is insoluble, or a swelling agent which is sparingly soluble in the presence of biological fluid and/or a swelling agent which is soluble or a gelling agent which is soluble in the presence of biological fluid, with, if need be, at least one excipient capable of improving bioadhesion and/or an auxiliary which is soluble in water or acts as an agent with a hydrophilic nature.

Advantageously, the bioadhesive material is essentially composed of a polymer modified by maleic anhydride or by a derivative such as a pharmaceutically acceptable acid, ester or salt.

It is preferably a copolymer of methylvinylether and maleic anhydride.

In the context of the invention, geared to the production of multilayer structures, this polymer is in fact used as a bioadhesive in its entirety, without it being necessary, as in the prior art, to mix it with other bioadhesives and/or for it to undergo particular treatments.

Examples of copolymers of this type which are currently available on the market correspond to those marketed under the trademark Gantrez® (GAF products).

They include Gantrez® AN (anhydride form), S (acid form), ES (ester form) and MS (sodium and calcium salt).

The swelling agents which are insoluble or the swelling agents which are sparingly soluble in the presence of biological fluid are advantageously chosen from the group of cellulose ethers such as sodium carboxymethylcellulose, crosslinked hydroxypropylcellulose, high molecular weight hydroxypropylcellulose, the group of enteric and non-enteric cellulose esters, modified starches such as carboxymethyl starch, the copolymer of divinylbenzene/potassium methacrylate, the group of derivatives of methacrylic acid such as polymethylmethacrylates, the group of crospovidones/crospolyvidones, high molecular weight polyvinyl alcohol, the group of alginic acid and derivatives thereof, the group of derivatives of acrylic acid such as crosslinked acrylic acid with divinylglycol and its calcium salt, the group of carrageenans and derivatives thereof, the copolymer of vinyl acetate and crotonic acid.

Swelling agents which are soluble or gelling agents which are soluble in the presence of biological fluid suitable for the exploitation of the invention include the group of cellulose ethers such as methylcellulose, sodium carboxymethylcellulose, low molecular weight hydroxypropylmethylcellulose, the group of enteric and non-enteric cellulose esters, low molecular weight polyvinyl alcohol, medium viscosity polyvinyl alcohol, polyoxyethylene glycol, the group of povidones/polyvidones/copolyvidones, scleroglucanes, starches and modified starches such as pregelatinised starches, the group of carrageenans and derivatives thereof, the group of alginic acid and derivatives thereof.

Other excipients used in association with the bioadhesive material may improve bioadhesion such as guar gum, xanthan gum, carob, carrageenates, pectin, a biological or synthetic protein used alone or in association with other proteins of biological or synthetic origin, cyclodextrins or derivatives such as betacyclodextrins, hydroxypropylbetacyclodextrins, partially methylated betacyclodextrins, derivatives of acrylic acid such as crosslinked acrylic acid with divinylglycol and its calcium salt.

Auxiliaries which are soluble in water or act as agents with a hydrophilic nature are chosen from lactose, mannitol, colloidal silicon dioxide, excipients of the group of hydrocelluloses such as microcrystalline cellulose, excipients in the group of cellulose ethers, gelatin, polyethylene glycols (PEG), poloxamers and pyrrolidones.

The bioadhesive layer advantageously contains 5 to 100% of bioadhesive material, 0 to 80% of insoluble swelling agent or sparingly soluble swelling agent, 0 to 50% of soluble swelling agent or of soluble gelling agent, 0 to 50% of excipient which, used in association with the bioadhesive polymer, may improve the bioadhesion, and 0 to 80% of water soluble auxiliary acting as an agent with a hydrophilic nature.

As has already been underlined, the production of such an adhesive layer makes it possible to limit the phenomenon of "sticking" of the tablet to a tissue other than that to which its application is desired. In fact, the presence of the bioadhesive polymer is limited to the surface in contact with the mucous membrane or the tissue. In the event of a buccoadhesive tablet, the presence of an adhesive layer greatly facilitates the placing of the tablet, limits the displacement thereof on the gum and on the lip during the initial stages of application, which improves bioadhesion and finally increases patient comfort. All these improvements mean that the risk hitherto of oral ingestion of the buccoadhesive tablet due to poor bioadhesion during the initial stages of application is very greatly reduced.

In the adhesive layer, it is also possible to add fatty bodies for reasons of pharmaceutical technology in proportions from 0 to 50% of the total mass of the layer. It is clear that this type of excipient with a hydrophobic nature is likely to affect the diffusion profiles of the active principle through the adhesive layer.

As regards the layer with the majority of the charge of active principle, also known hereinafter as the main layer, it contains advantageously, in mixture with the active principle (s), at least one swelling agent which is insoluble or a swelling agent which is sparingly soluble in the presence of biological fluid and/or at least one swelling agent which is soluble or a gelling agent which is soluble in the presence of biological fluid with, if need be, at least one excipient which makes it possible to obtain inclusions of active principle and/or at least one excipient which is soluble in water or acts as an agent with a hydrophilic nature, or at least one excipient which is insoluble in water or acts as an agent with a hydrophobic nature.

The agents already mentioned in relation to the adhesive layer are chosen preferably from the products respectively indicated above for each type of agents.

The excipients that make it possible to obtain inclusions of active principle include, for example, cyclodextrins or derivatives such as betacyclodextrins, hydroxypropyl-betacyclodextrins, partially methylated betacyclodextrins and glycerides such as glyceryl mono-oleate.

The auxiliaries which are insoluble in water or act as agents with a hydrophobic nature are chosen in particular from hydrogenated castor oil, magnesium stearate, natural and synthetic oils, natural or semi-synthetic waxes, esters of fatty acids and of polyoxyethylene, fatty acids and esters of fatty acids (mono and triglycerides) and derivatives thereof such as polyethoxylated fatty acids (PEG stearate, . . .) fatty alcohols and esters of fatty alcohol and derivatives thereof such as polyethoxylated fatty alcohols (octyldodeceth-25, . . .) and polyvinyl chloride.

The active principle(s) are chosen in particular from an antihistamine, an anticholinergic, a mineral element, an allergen, a local or general surface anaesthetic, an antipyretic, a non-opiate antalgic, an opiate antalgic, an anticholinergic and non-anticholinergic antispasmodic, a non-steroidal anti-inflammatory such as taiprofenic [sic] acid, indomethacin, diclofenac, ibuprofen, ketoprofen, naproxen, piroxicam, a steroidal anti-inflammatory such as betamethasone, prednisolone, a cyctotoxic agent, an antihormonal agent, an antianaemic, an antiemetic, an antiasthenic, an antihypertensive and, of these, the beta-blocking agents such as propanolol, atenolol, metoprolol, conversion enzyme inhibitors such as captopril, enalapril, angiotensin II antagonists, calcium antagonists such as nifedipine and diltiazem, central action antihypertensives, vasodilators, a hypolipemic, an oral antidiabetic, an anticoagulant, an antiplatelet drug, a calcium antagonist, a nitrate derivative used in the treatment of coronary insufficiency, a non-nitrate antianginal, a diuretic, a derivative of digitalin and allied products, an antiarrythmic, an antihypotensive and circulatory analeptic, a vasodilator, an antiischaemic, a vasculoprotector and a veinotonic, a hormone, an antiherpetic, an antiphotosensitiser, an antiulcer drug such as ranitidine, cimetidine, an antacid, a laxative, an antidiarrhoeal, an antifungal, a cholelitholytic, an interferon, an enzyme, an antispasmodic, an antibacterial, an antiseptic, an antiherpetic, a uturorelaxant, an oxytocic, an oestrogen, a progestogen, an oestroprogestogen, an active principle indicated in lactation such as bromocryptine, an active principle indicated in the treatment of sterility, an antigonadotropin, an anticoagulant, a thrombolytic, an antifibrinolytic, a vitamin, a haemostatic, a cyclosporin, an alkylating agent, an antibiotic, an antiviral, an antiparasitic, a vaccine, a diagnostic product, an active principle indicated in the treatment of obesity, an orexigenic, an active principle indicated in the treatment of corrections of metabolic anomalies, an active principle indicated in oral and enteral nutrition, an anticonvulsant, an antiparkinsonian drug, an antimyasthenic, an active principle indicated in the treatment of Alzheimer's disease, an antimigraine agent, a neuroleptic, an anxiolytic, a hypnotic, a sedative, an antidepressant, a normothymic, a psychostimulant, an active principle indicated in the treatment of dependency states in alcohol science, tobacco detoxification, opiate detoxification, an antiglaucoma agent, a mydriatic agent, a bronchodilator, an antiasthmatic, an antitussive, a bronchial expectorant, a (topical) counter-irritant, an active principle indicated in the treatment of osteopathies, an active principle indicated in the treatment of acute attacks of gout, an active principle indicated in the treatment of hypouricaemia, an active principle indicated in the treatment of algodystrophies, a muscle relaxant, an active principle indicated in the treatment of osteoarthritis, a corrector of hyposalivation, an active principle indicated in the treatment of urinary lithiasis, an active principle indicated in the treatment of renal insufficiency, an active principle indicated in the treatment of enuresis, an active principle indicated in the treatment of retrograde ejaculation, an active principle indicated in the treatment of impotence, and others.

The molecules contained in the composition according to the invention include contrast agents, radioelements, minerals and colouring agents, the list being non-limiting.

The main layer contains advantageously 70 to 100% of the total charge of active principle of the tablet, 0 to 50% of insoluble swelling agent or of sparingly soluble swelling agent, 0 to 50% of soluble swelling agent or of soluble gelling agent, 0 to 50% of excipient which allows inclusions of active principle to be obtained, 0 to 50% of water-soluble auxiliary acting as an agent with a hydrophilic nature, 0 to 50% of water-insoluble auxiliary acting as an agent with a hydrophobic nature.

As indicated above, according to a provision of the invention, the multilayer tablets contain at least one barrier.

The barrier layer(s) are essentially formed from the active principle in a proportion that may range from 0 to 30% of the total charge of at least one swelling agent which is insoluble or a swelling agent which is sparingly soluble in the presence of biological fluid and/or a swelling agent which is soluble or a gelling agent which is soluble in the presence of biological fluid with, if need be, at least one excipient which allows inclusions of active principle to be obtained, and/or an auxiliary which is soluble in water or acts as an agent with a hydrophilic nature and/or at least one agent which is insoluble in water or acts as an agent with a hydrophobic nature.

These various agents are advantageously chosen from the compounds given above in relation to each type.

The barrier layer advantageously contains 0 to 30% of the total charge of active principle of the tablet, 0 to 80% of insoluble swelling agent or sparingly soluble swelling agent, 0 to 80% of soluble swelling agent or soluble gelling agent, 0 to 50% of excipient which allows inclusions of active principle to be obtained, 0 to 25% of auxiliary which is soluble in water or acts as an agent with a hydrophilic nature, 0 to 50% of auxiliary which is insoluble in water and acts as an agent with a hydrophobic nature.

The three types of layers above also include, if need be, other excipients or substances chosen from those acting as:
  diluents, such as lactose and derivatives thereof or dicalcium dihydrogen phosphate, microcrystalline cellulose and its compound products such as the combination of microcrystalline cellulose and colloidal silicon dioxide (Prosolv SMCC from Mendell), starches and derivatives thereof such as pregelatinised starches;
  binders such as povidone and polyvidone, ethylcellulose, alginic acid and derivatives thereof, maltodextrins, anhydrous or modified crystalline lactose monohydrate or which is contained in a compound product such as compounds formed from lactose and microcrystalline cellulose, microcrystalline cellulose and its compound products such as the combination of microcrystalline cellulose and colloidal silicon dioxide (Prosolv SMCC from Mendell), partially substituted hydroxypropylcellulose, starches and derivatives thereof such as pregelatinised starches, talc;
  lubricants, such as magnesium stearate, esters of fatty alcohol, esters of fatty acids, sodium stearyl fumarate, hydrogenated vegetable oils, derivatives of polyethylene glycol;
  flow improvers such as colloidal silicon dioxides, modified starches such as pregelatinised starch;
  flavour masking agents such as certain derivatives of methacrylic acid;
  agents involved in maintaining the cohesion and general appearance of the tablet, that is, excipients or substances that make it possible to monitor the development of the tablet in situ so as to avoid, for example, phenomena of cleavage, the formation of holes, phenomena of non-homogeneous swelling between the various layers of the tablet.

It is also possible to incorporate in them
  absorption promoters,
  solubilising agents such as polysorbates, pyrrolidones, derivatives of polyethylene glycols, derivatives of propylene glycol and glycerol, derivatives of polyethylene glycol such as glycerol polyethylene glycol hydroxystearate,
  aromatisers
  colouring agents
  sweeteners
  plasticisers
  antioxidants
  disintegrating agents such as sodium croscarmellose, sodium carboxymethyl starch, partially substituted hydroxypropylcellulose, crospovidone, sodium starch glycollate,
  laminating agents, coating agents, film-forming agents such as hydroxypropyl-cellulose, derivatives of methacrylic acid, the copolymer of vinyl acetate and crotonic acid,
  agents contained in the composition of the polishing and gloss-enhancing solution,
  agents that protect the active principle from heat such as sucrose derivatives.

The various layers constituting the tablet may contain coated or uncoated microcapsules or nanoparticles or nanogranules or nanocapsules.

It will be appreciated that the tablets of the invention may have particular structures (relative arrangement of the layers) which make it possible to orientate the flow of active principles towards the desired route(s) of administration.

The compound(s) present in the adhesive layer (apart from the bioadhesive compound proper) may be identical to or different from the compound(s) present in the main layer of the tablet. The compound(s) of the adhesive layer are preferably medium or high viscosity hydroxypropylmethylcellulose(s) (HPMC) such as Methocel K 15M and K 100M P (COLORCON). Advantageously, this excipient is involved in the phenomenon of bioadhesion, because it makes it possible to establish a hydrogel, the swelling of which is gradual, which promotes long-term bioadhesion.

If it is desired to obtain short-term adhesion, a low viscosity hydroxypropylmethylcellulose or a maize starch or any other excipient is chosen from the compounds mentioned in the composition of the adhesive layer.

If it is desired to obtain a gradual and constant release of the active principle, it is preferable to choose the same excipient(s) assuring controlled release for the main layer and the adhesive layer of the tablet, in so far as the compound chosen makes it possible to obtain, when it is combined with a bioadhesive polymer, a bioadhesion corresponding to the desired application time.

If the aim is to obtain a rapid release profile of the active principle (plasma peak), followed by a prolonged and constant release of the active principle, the non-bioadhesive excipient(s) present in the adhesive layer are chosen for their ability to form a hydrogel rapidly and for their compatibility with the bioadhesive polymer. The non-bioadhesive compound(s) that make up the main layer of the tablet are chosen such as to promote the release of the active principle by the oral route by one or more phenomena of promoted diffusion (porosity), disintegration and others.

The rapid or slow release profiles are also obtained by combining or not combining the description above with a particular pharmaceutical technology for the production of layers.

The rapid release profiles are obtained preferably by direct compression and the slow profiles by a process of wet granulation of the main layer and/or of the barrier layer.

Preferred tablets containing at least one barrier layer are three-layer tablets produced for use essentially by the transmucosal route, in which the internal layer of active principle is covered on its two opposite faces, respectively with the bioadhesive layer and the barrier layer, and on the sides, either with the bioadhesive layer or with the barrier layer, or is covered on both faces with the bioadhesive layer and on its sides with the barrier layer.

As a variant, the tablets of the invention are produced for a use by an essentially non-transmucosal route and are formed successively from an external bioadhesive layer, a barrier layer, a layer of active principle, said layers being superposed or the layer of active principle being, if need be, covered on at least one side with the barrier layer, or the layer of active principle being covered on its external face with a barrier layer.

According to another variant, the tablets of the invention are produced for use by a mixed route, transmucosal or non-transmucosal, and comprise the bioadhesive layer, with the active principle and the barrier layer, superposed, either the barrier layer on one or both sides of the layer of active principle, or both external opposite bioadhesive layers with an internal barrier and an internal layer of active principle.

Particularly suitable dimensions in view of the applications envisaged correspond to a width of about 2 to 30 mm and a thickness of about 1 to 5 mm.

Generally speaking, the tablets as defined above may exhibit a flat, semi-convex, oblong, parallepipedic, chambered or non-chambered format or any geometric shape that has the advantage of ensuring the best prolonged maintenance of the tablet on its site of action. Said tablets may be divisible. They may be pierced.

Said tablets may contain coated or uncoated minigranules, microcapsules, nanoparticles or nanocapsules.

The new tablets according to the invention have medical, therapeutic or preventive or health applications in man or animals. They may be used advantageously for oral, perlingual administration, administration across the buccal mucosa (throat or gums), for vaginal, anal, nasal, rectal administration or in the gastrointestinal tract or on an internal organ by surgery. Depending on their structure, the release of active principle may or may not take place systemically. It will be noted that the pharmaceutical forms with small dimensions are particularly suitable for applications in ophthalmology on the conjunctiva of the eye, particularly the conjunctival cul de sac, and the cornea.

The tablet may also be used by virtue of its bioadhesive nature as a bioadhesive support integrated in a therapeutic or health process. For example, the tablet may be loaded with a compound making it possible to set up a localised magnetic field (thanks to the bioadhesion). This magnetic field, when active, allows the functioning of a second pharmaceutical form and localised release of substance in one place and at one time.

The invention also relates to a process for the preparation of the tablets defined above.

The process is characterised in that it comprises:
the direct compression of the mixture of ingredients produced to form the bioadhesive layer;
the direct compression of the mixture of ingredients produced to form the layer of active principle and of that produced to form the barrier layer, or the compression of one of these mixtures or of both mixtures as obtained by granulation by the wet method or by dry granulation.

Other characteristics and advantages of the invention will be given in the Examples that follow, with reference to FIGS. 1 to 3 which represent, respectively:

BRIEF DESCRIPTION OF THE DRAWINGS

FIGS. 1A to 1C, relative arrangements of layers which may adapted to an essentially transmucosal route;

Figure 2A:
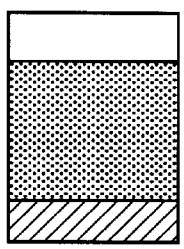
FIGS. 2A to 2F, relative arrangements of layers which may be adapted to a mixed transmucosal/non-transmucosal route, and FIGS. 3A to 3D, relative arrangements of layers which may be adapted to an essentially non-transmucosal route.

For each of these Figures, the corresponding legend is:

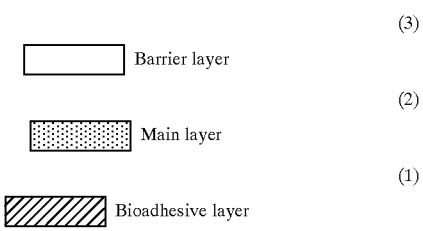

EXAMPLE 1 a) Preparation of Mixtures Used to Form the Various Layers

Mixture A used to form the layer with the active principle or the main layer:

The following excipients are weighed out in order to produce the equivalent of 100 main layers.

| Excipients | Quantities |
|---|---|
| Melatonin (Sigma) | 0.3 g |
| Ethylcellulose (Ethylcellulose NF 100 - Aqualon) | 0.5 g |
| Dicalcium dihydrogen phosphate (Encompress - SPCI) | 6.1 g |
| Hydroxypropylmethylcellulose (Methocel K100M - Colorcon) | 3.0 g |
| Magnesium stearate (Lambert Rivière) | 0.1 g |

The melatonin, dicalcium phosphate and half the quantity of ethylcellulose are mixed in the Turbula for 10 minutes. The mixture is screened through a sieve with a sieve opening of 0.8 mm. The remainder of the ethylcellulose is dissolved in 5 ml of ethanol. The mixture is granulated with this alcoholic solution of ethylcellulose with a Kitchen Aid at speed 2 for 10 minutes. The mass obtained is calibrated on a sieve with a sieve opening of 0.8 mm. After being dried, the granules are screened (sieve opening: 0.4 mm). The hydroxypropylmethylcellulose and the granules obtained are mixed. The magnesium stearate is then added and the mixture is then homogenised.

Mixture B used to form the bioadhesive layer:

The following excipients are weighed out in order to produce the equivalent of 100 bioadhesive layers.

| Excipients | Quantities |
|---|---|
| Copolymer of methylvinylether and maleic anhydride (Gantrez MS 955 - ISP) | 4.87 g |

-continued

| Excipients | Quantities |
| --- | --- |
| Hydroxypropylmethylcellulose (Methocel K100M - Colorcon) | 4.87 g |
| Magnesium stearate (Lambert Rivière) | 0.1 g |
| Colloidal silicon dioxide (Lambert Rivière) | 0.06 g |
| Yellow iron oxide (Sicovit) (BASF) | 0.1 g) |

The products may be mixed directly before compression.

The copolymer of methylvinylether and maleic anhydride is mixed with the hydroxypropylmethylcellulose in a Turbula for 10 minutes. The magnesium stearate, colloidal silicon dioxide and the yellow iron oxide are added and the mixture as a whole is mixed in the Turbula for 4 minutes.

Mixture C used to form the barrier layer:

The following excipients are weighed out in order to produce the equivalent of 100 barrier layers.

| Excipients | Quantities |
| --- | --- |
| Ethylcellulose (Ethylcellulose NF 100 - Aqualon) | 0.9 g |
| Dicalcium dihydrogenphosphate (Encompress - SPCI) | 6.9 g |
| Hydroxypropylmethylcellulose (Methocel K100M - Colorcon) | 2.0 g |
| Magnesium stearate (Lambert Rivière) | 0.1 g |
| Red iron oxide (BASF) | 0.1 g |

The quantity of ethylcellulose is divided into two equal fractions. A first fraction is mixed in the Turbula for 10 minutes with all the dicalcium hydrogenphosphate. The mixture obtained is screened through a sieve with a sieve opening of 0.8 mm. The remainder of the ethylcellulose is dissolved in 5 ml of ethanol. The previous mixture is granulated with this alcoholic solution of ethylcellulose in a Kitchen Aid at speed 2 for 10 minutes. The mass is calibrated on a sieve with a sieve opening of 0.8 mm. After being dried, the granules are screened (sieve opening: 0.4 mm). The hydroxypropylmethylcellulose is mixed with the granules. The magnesium stearate and red iron oxide are then added and the mixture is then homogenised in the Turbula for 4 minutes.

b) Compression Stage

The compression operations are carried out manually on an EKO type KORSH alternating compressing machine so as to obtain flat round tablets. The thickness of the tablets is 2 mm and their diameter is 10 mm.

The compression of 100 mg of mixture A corresponding to the main layer is carried out in a die with a flat format with a diameter of 8 mm. The tablets obtained are recovered.

The 10 mm format die is filled with 50 mg of mixture C and compressed lightly.

The tablet with an 8 mm diameter format is placed centrally in the compression chamber. The chamber is filled with the remaining 50 mg of mixture C. The mixture is levelled off to the upper level of the tablet and compressed lightly.

The compression chamber is then fed with 100 mg of mixture B. The mixture is levelled off and the final compression carried out.

A finished 300 mg flat tablet is obtained. It has the structure illustrated by FIG. 1A with a bioadhesive layer (1) and a main layer (2) covered on its sides and surface with a barrier layer (3).

It is also possible, by operating with mixture B in the first and last stage and by placing mixture C solely on the sides according to the method detailed above, to obtain the structure illustrated by FIG. 1B which comprises two external bioadhesive layers (1) trapping a layer of active principle (2), the sides of which are covered with barrier layer (3).

As a variant, a tablet of the kind represented in FIG. 1C is produced by filling the compression chamber with 50 mg of mixture B which is compressed, then placing in the centre of the die the tablet produced beforehand with mixture A, then adding around the tablet 50 mg of mixture B which is compressed to form the bioadhesive layer (1) Mixture C is then introduced into the hopper to form the barrier layer (3).

The tablet may be placed on the gingival mucosa of a patient and may release melatonin in a controlled manner for 8 hours without disintegrating, without deadhering and without sticking in an inappropriate manner. Such a design permits the release of melatonin by an essentially transmucosal route and a use of active principle and excipients in a reduced quantity.

EXAMPLE 2 a) Preparation of Mixtures A, B and C

In order to prepare mixture A, the following excipients are weighed out in order to produce the equivalent of 100 main layers.

| Excipients | Quantities |
| --- | --- |
| Piroxicam (Schweizerhall) | 1.0 g |
| Ethylcellulose (Ethylcellulose NF 100 - Aqualon) | 0.25 g |
| Dicalcium dihydrogenphosphate (Encompress - SPCI) | 2.2 g |
| Hydroxypropylmethylcellulose (Methocel K100M - Colorcon) | 1.5 g |
| Magnesium stearate (Lambert Rivière) | 0.05 g |

The same procedure as in Example 1 is then followed in order to carry out mixing of the excipients, screening, granulation, calibration, drying and screening, to obtain a granulometry of 0.4 mm.

Similarly, the bioadhesive layer (mixture B) and barrier layer (mixture C) are prepared as indicated in Example 1. The excipients are identical but the quantities are to be divided by two, as are the quantities of alcohol to be used for wet granulation.

b) Compression Stage

The compression operations are carried out manually on an EKO type KORSH compressing machine so as to obtain circular flat tablets.

Mixture C is precompressed and forms a barrier layer (3).

The compression chamber is then filled with mixture A containing the active principle (piroxicam). Precompression forms the layer with the active principle (2) above the barrier layer.

The die is then fed with mixture B (bioadhesive layer) which is placed above the layer with the active principle. Final compression results in a circular flat tablet (about 8 rnm in diameter) weighing about 150 mg.

It has the structure illustrated by FIG. 2A with the layers (1), (2) and (3) superposed.

Figure 2B:
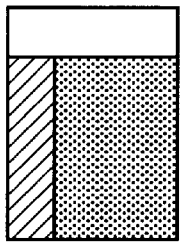
Figure 2E:
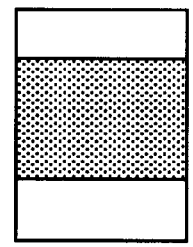
Figure 2C:
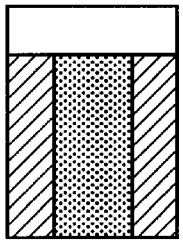

It is also possible to obtain the structures illustrated by FIG. 2B which contains the barrier layer on one side and FIG. 2C which contains the barrier layer respectively on the two sides of the main layer and not on its external face.

FIG. 2B can be obtained by placing the tablet produced beforehand with mixture A (diameter 6 mm) in an offset manner in the die (against the edge of the compression chamber).

Figure 2F:
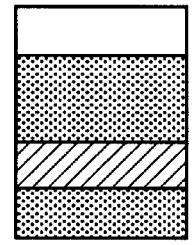
Figure 2D:
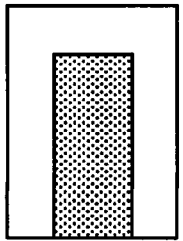

FIG. 2C is obtained according to the method in Example 1 for FIG. 1C so as to form a barrier layer (3) on both sides. According to another variant, a structure such as the one represented in FIG. 2D is produced. Operations are carried out as explained in FIG. 2C but the barrier layer is replaced by a bioadhesive layer.

FIG. 2E is obtained according to the method explained for FIG. 2A but in this case, the barrier layer is replaced by a bioadhesive layer. There is also a variant of FIG. 2E which is FIG. 2F which superposes a bioadhesive layer, a main layer a barrier layer, and another main layer.

The tablet may then be placed on the gingival mucosa of a patient suffering from an inflammatory rheumatic complaint. It can release piroxicam in a controlled manner for 6 hours without deteriorating.

EXAMPLE 3 a) Preparation of Mixtures A, B and C

Mixtures A, B and C are prepared by proceeding as described in Example 1, mixture A being obtained from the following excipients used in quantities which make it possible to produce the equivalent of 100 main layers.

| Excipients | Quantities |
| --- | --- |
| Betamethasone (SIGMA) | 0.025 g |
| Ethylcellulose (Ethylcellulose NF 100 - Aqualon) | 0.25 g |
| Dicalcium dihydrogenphosphate (Encompress - SPCI) | 3.175 g |
| Hydroxypropylmethylcellulose (Methocel K100M - Colorcon) | 1.5 g |
| Magnesium stearate (Lambert Rivière) | 0.05 g |

Similarly, the bioadhesive layer (mixture B) and the barrier layer (mixture C) are prepared as indicated in Example 1. The excipients are identical but the quantities are to be divided by two, as are the quantities of alcohol to be used for wet granulation.

b) Compression Stage

The compression operations are carried out manually on a compressing machine so as to obtain parallepipedic flat tablets.

Mixture B is compressed lightly to form a layer (bioadhesive layer).

A fraction of mixture C is placed on the adhesive layer. Precompression forms a barrier layer above the bioadhesive layer.

A tablet produced beforehand with mixture A (betamethasone) is then placed in position. This tablet, which has a diameter of 6 mm, is placed in the centre of the compression chamber. The die is filled with mixture C as far as the upper level of the tablet. Final compression completes the tablet.

Figure 3A:
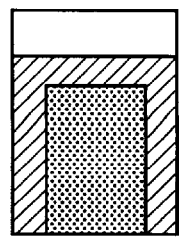

A tablet weighing about 150 mg is obtained, which has the structure illustrated by FIG. 3A with a bioadhesive layer (1), a barrier layer (2) and a main layer (3), the sides of which are covered with the barrier layer.

Figure 3B:
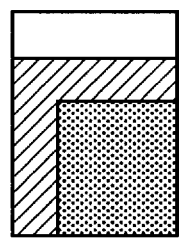
Figure 3C:
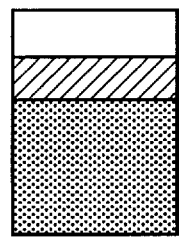
Figure 3D:
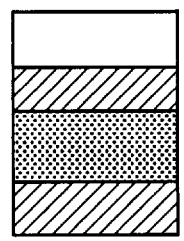

It is also possible to obtain the design illustrated by FIG. 3B by placing the tablet formed from mixture A with a diameter of 6 mm in an offset manner.

As a variant, mixtures A, C, and B are introduced and compressed successively, giving structure 3C, or again structure 3D if an additional input of mixture C is used to form another barrier layer (3).

The tablet may then be placed on the buccal mucosa of a patient having aphthous ulcers. It can release betamethasone in a controlled manner for 4 hours without deteriorating.

Such a design permits an essentially non-transmucosal release, i.e. by a local route.

Such a design permits rapid release of the active principle by the oral route and prolonged release through the mucous membranes. Such a tablet permits, therefore, the continuous release of active principle for 2 hours into the plasma from reduced quantities of active principle. Flavouring or masking agents may advantageously be incorporated in order to improve the patient's comfort.

The same type of tablet may be produced with other active principles, vitamins, amino acids, and hormones, for example.

EXAMPLE 4 a) Preparation of Mixtures A, B and C

Mixtures A and B are prepared by proceeding as in Example 1 but using, for mixture A, the following excipients according to the quantities indicated which make it possible to produce the equivalent of 100 main layers.

| Excipient | Quantities |
| --- | --- |
| Prochlorperazine (RPR) | 0.5 g |
| Ethylcellulose (Ethylcellulose NF 100 - Aqualon) | 0.25 g |
| Dicalcium dihydrogenphosphate (Encompress - SPDI) | 2.7 g |
| Hydroxypropylmethylcellulose (Methocel K100M - Colorcon) | 1.5 g |
| Magnesium stearate (Lambert Rivière) | 0.05 g |

In order to prepare mixture C, the following excipients are used to produce the equivalent of 100 barrier layers.

| Excipients | Quantities |
| --- | --- |
| Hydroxypropylcellulose (Klucel - Aqualon) | 1.0 g |
| Dicalcium dihydrogenphosphate (Encompress - SPCI)) | 2.8 g |
| Polyvinylpyrrolidone (Plasdone K29-32 - ISP) | 0.1 g |
| Hydroxypropylmethylcellulose (Methocel K100M - Colorcon) | 1.0 g |
| Magnesium stearate (Lambert Rivière) | 0.05 g |
| Red iron oxide (Sicovit - BASF) | 0.05 g |

The hydroxypropylcellulose is mixed with the dicalcium phosphate in a Turbula for 10 minutes. The mixture obtained is screened over a 0.8 mm sieve. All the polyvinylpyrrolidone is dissolved in 3.5 ml of water. The previous mixture is granulated with this solution in a Kitchen Aid at speed 2 for 8 minutes. The mass is calibrated on a sieve with a sieve opening of 0.8 mm. After being dried, the granules are screened over a 0.4 mm sieve. The hydroxypropylmethyl cellulose is mixed with the granules in a Turbula for 10 minutes, then the magnesium stearate and red iron oxide are added and the mixture is homogenised in the Turbula for 4 minutes.

b) Compression Stage

The compression operations are carried out on an EKO type KORSH alternating compressing machine so as to obtain round flat tablets.

A round flat tablet with a diameter of 6 mm is obtained from mixture A (main layer).

The compression chamber is filled with 50 mg of mixture C. Precompression is carried out (barrier layer). The tablet obtained is placed with mixture A above the barrier layer in the centre of the die. The die is then filled with 50 mg of mixture B so as to cover the tablet forming the main layer containing the active principle (prochlorperazine). Final compression is carried out.

A round flat tablet with a diameter of 8 mm is obtained weighing about 150 mg which has the design illustrated by FIG. 1C. The tablet may be placed inside a cavity of a buccal mucosa of a patient suffering from nausea and vomiting. It can release prochlorperazine in a controlled manner for 5 hours without deteriorating. Such a design permits prolonged release essentially by the transmucosal route.

EXAMPLE 5 a) Preparation of Mixtures A, B and C

Mixtures A and B are prepared by proceeding as in Example 1 but using, for mixture A, the following excipients, according to the quantities indicated which make it possible to produce the equivalent of 100 main layers.

| Excipients | Quantities |
| --- | --- |
| Nifedipine (SIGMA) | 0.8 g |
| Microcrystalline cellulose (Avicel PH 302 - SEPPIC) | 0.2 g |
| Lactose Fast Flo (SEPPIC) | 1.975 g |
| Hydroxypropylmethylcellulose (Methocel K4M - Colorcon) | 0.5 g |
| Hydroxypropylmethylcellulose (Methocel K100M - Colorcon) | 1.5 g |
| Magnesium stearate (Lambert Rivière) | 0.025 g |

The excipients, except for magnesium stearate, are mixed in the Turbula for 10 minutes. The mixture obtained is screened on a 0.8 mm sieve. The magnesium stearate is then added and the mixture is then mixed in the Turbula for 4 minutes.

In order to prepare mixture B:

The following excipients are weighed out in order to produce the equivalent of 100 bioadhesive layers.

| Excipients | Quantities |
| --- | --- |
| Copolymer of methylvinylether and maleic anhydride (Gantrez MS 955 - ISP) | 2.435 g |
| Hydroxypropylmethylcellulose (Methocel K100M - Colorcon) | 2.435 g |
| Magnesium stearate (Lambert Rivière) | 0.05 g |
| Colloidal silicon dioxide (Lambert Rivière) | 0.03 g |
| Yellow iron oxide (Sicovit) (BASF) | 0.05 g |

In order to prepare mixture C, the following excipients are used to produce the equivalent of 100 barrier layers.

| Excipients | Quantities |
| --- | --- |
| Glyceryl monostearate (Myvaplex 600 - Unipex) | 1.0 g |
| Hydroxypropylmethylcellulose (Methocel K100M - Colorcon) | 3.95 g |
| Red iron oxide | 0.05 g |

The glyceryl monostearate is mixed with the hydroxypropylcellulose in the Turbula for 5 minutes. The mass is calibrated on a screen with a mesh size of 0.8 mm. The red iron oxide is added and the mixture mixed in the Turbula for 4 minutes.

b) Compression Stage

The compression operations are carried out on an EKO type KORSH alternating compressing machine so as to obtain round flat tablets.

A round flat tablet with a diameter of 6 mm is obtained from mixture A (main layer).

The compression chamber is filled with 50 mg of mixture C. Precompression is carried out (barrier layer). The tablet produced with mixture A is placed on top of the barrier layer in the centre of the die. The die is then filled with 50 mg of mixture B so as to cover the tablet forming the main layer containing the active principle (nifedipine). Final compression is carried out.

A round flat tablet weighing about 150 mg is obtained, which has the design illustrated by FIG. 1C.

The tablet may be placed on the buccal mucosa of a patient undergoing treatment for hypertension by replacing the treatment by the sublingual route, where it will release trinitrin in a controlled manner for 2 hours without deteriorating. Such a design permits rapid release of active principle by the transmucosal route.

EXAMPLE 6 a) Preparation of Mixtures A, B and C

Mixtures A and B are prepared by proceeding as in Example 5 but using, for mixture A, the following excipients according to the quantities indicated which make it possible to produce the equivalent of 20,000 main layers.

| Excipients | Quantities |
| --- | --- |
| Melatonin (SIGMA) | 60.0 g |
| Microcrystalline cellulose (Avicel PH 302 - SEPPIC) | 140.0 g |
| Lactose Fast Flo (SEPPIC) | 395.0 g |
| Hydroxypropylmethylcellulose (Methocel K4M - Colorcon) | 100.0 g |
| Hydroxypropylmethylcellulose (Methocel K100M - Colorcon) | 300.0 g |
| Magnesium stearate (Lambert Rivière) | 5.0 g |

The excipients, except for magnesium stearate, are mixed in the OURS type 10 litre planetary mixer for 10 minutes at a speed of 35%. The mixture obtained is screened over a 0.8 mm sieve. The magnesium stearate is then added and mixed in the OURS for 4 minutes at a speed of 35%.

In order to prepare mixture B:

The following excipients are weighed out in order to produce the equivalent of 20,000 bioadhesive layers.

| Excipients | Quantities |
| --- | --- |
| Copolymer of methylvinylether and maleic anhydride (Gantrez MS 955 - ISP) | 487.0 g |
| Hydroxypropylmethylcellulose (Methocel K100M - Colorcon) | 487.0 g |
| Magnesium stearate (Lambert Rivière) | 10.0 g |
| Colloidal silicon dioxide (Lambert Rivière) | 6.0 g |
| Yellow iron oxide (Sicovit) (BASF) | 10.0 g |

The products may be mixed directly before compression.

The copolymer of methylvinylether and maleic anhydride is mixed with the hydroxypropylmethylcellulose in an OURS type planetary mixer for 10 minutes at a speed of 35%. The magnesium stearate, colloidal silicon dioxide and yellow iron oxide are added, and the whole mixture is mixed in the OURS mixer for 4 minutes.

In order to prepare mixture C, the following excipients are used to produce the equivalent of 20,000 barrier layers.

| Excipients | Quantities |
|---|---|
| Glyceryl monostearate (Myvaplex 600 - Unipex) | 200.0 g |
| Hydroxypropylmethylcellulose (Methocel K 100M - Colorcon) | 790.0 g |
| Red iron oxide | 10.0 g |

The glyceryl monostearate is mixed with the hydroxypropylcellulose in the OURS type planetary mixer for 10 minutes at a speed of 35%. The mixture is calibrated on a sieve with a sieve opening of 0.8 mm. The red iron oxide is added and mixed in the OURS mixer for 4 minutes.

b) Compression Stage

Compression is carried out on a multilayer machine (Manesty, Liverpool). The machine is fitted with a flat format 8 mm in diameter. The machine is regulated so as to deliver mixture C (barrier layer) on line 1, mixture A (main layer) on line 2, and mixture B (bioadhesive layer) on line 3. The machine is calibrated to deliver 50 mg of direct compression mixture per line. The force of the final compression is 3,000 kg/cm². The rate of compression is 20,000 tablets/hour.

A round flat tablet weighing about 150 mg is obtained, which has the design illustrated by FIG. 2A.

The tablet may be placed on the buccal mucosa to regulate sleep in shift workers. The tablet ensures the release of melatonin in a controlled manner for 4 hours without deteriorating. Such a design permits the rapid release of active principle by a non-transmucosal route and a prolonged transmucosal release of melatonin.

EXAMPLE 7 a) Preparation of Mixtures A, B and C

Mixtures A and B are prepared by proceeding as in Example 6 but using, for mixture A, the following excipients according to the quantities indicated which make it possible to produce the equivalent of 10,000 main layers.

| Excipients | Quantities |
|---|---|
| Melatonin (SIGMA) | 30.0 g |
| Microcrystalline cellulose (Avicel PH 302 - SEPPIC) | 70.0 g |
| Lactose Fast Flo (SEPPIC) | 197.5 g |
| Hydroxypropylmethylcellulose (Methocel K4M - Colorcon) | 50.0 g |
| Hydroxypropylmethylcellulose (Methocol K100M - Colorcon) | 150.0 g |
| Magnesium stearate (Lambert Rivière) | 2.5 g |

In order to prepare mixture B:

The following excipients are weighed out in order to produce the equivalent of 10,000 bioadhesive layers.

| Excipients | Quantities |
|---|---|
| Copolymer of methylvinylether and maleic anhydride (Gantrez MS 955 - ISP) | 243.5 g |
| Hydroxypropylmethylcellulose (Methocel K100M - Colorcon) | 243.5 g |
| Magnesium stearate (Lambert Rivière) | 5.0 g |
| Colloidal silicon dioxide (Lambert Rivière) | 3.0 g |
| Yellow iron oxide (Sicovit) (BASF) | 5.0 g |

The products may be mixed directly before compression.

The copolymer of methylvinylether and maleic anhydride is mixed with the hydroxypropylmethylcellulose in the Turbula for 10 minutes. The magnesium stearate, colloidal silicon dioxide and yellow iron oxide are added, and the whole mixture is mixed in the Turbula for 4 minutes.

In order to prepare mixture C, the following excipients are used to produce the equivalent of 10,000 barrier layers.

| Excipients | Quantities |
|---|---|
| Glyceryl monostearate (Myvaplex 600 - Unipex) | 100.0 g |
| Hydroxypropylmethylcellulose (Methocel K100M - Colorcon) | 395.0 g |
| Red iron oxide (BASF) | 5.0 g |

The glyceryl monostearate is mixed with the hydroxypropylcellulose in the Turbula for 10 minutes. The mixture is calibrated on a sieve with a sieve opening of 0.8 mm. The red iron oxide is added, and the mixture is mixed in the Turbula for 4 minutes.

b) Compression Stage

Compression is carried out on a multilayer machine (Manesty, Liverpool). The machine is fitted with a flat format 3 mm in diameter and 1.0 mm thick. The machine is regulated so as to deliver mixture C (barrier layer) on line 1, mixture A (main layer) on line 2, and mixture B (bioadhesive layer) on line 3. The machine is calibrated to deliver 10 mg of direct compression mixture per line. The force of the final compression is 2,500 kg/cm². The rate of compression is 10,000 tablets/hour.

A round flat tablet weighing about 30 mg is obtained, which has the design illustrated by FIG. 2A.

The tablet may be placed on the conjunctival cul de sac of the eye and makes it possible to release timolol by a non-transmucosal route which is used in the treatment of glaucoma. The tablet ensures prolonged release of the active principle in the same way as the gels currently in use.

The invention thus provides highly effective bioadhesive tablets which have optimum flexibility of application.

They have, in particular, very low risks of accidental detachment and overdosing which may be associated with them. They have the advantage of maintaining adhesion between the various layers and of having a homogeneous distribution of the stresses which result from changes in the level of hydration of the various layers. They do not, therefore, have the disadvantages associated with the splitting of layers such as premature or excessive release of active principles.

Moreover, they give rise neither to discomfort due to bulk, nor to allergies, sensitisation or irritation (the effects of the active principle(s) alone not, of course, being considered).

What is claimed is:

1. A bioadhesive tablet, in the form of multilayers comprising at least one bioadhesive layer having a directly compressed structure and containing the total charge of a bioadhesive material that is essentially composed of a product selected from the group consisting of polymers modified by maleic anhydride and pharmaceutically acceptable derivatives thereof, said bioadhesive layer adhering, in operation to a biological tissue or a mucous membrane by impregnation with water or with the biological fluid present in the environment of the tissue or mucous membrane, and permitting the release, as desired, of active principle, and at least one layer containing the majority of the total charge of active principle.

2. The tablet according to claim 1, further comprising at least one layer forming a barrier to diffusion of active principle and to the penetration of water or of said biological fluid.

3. The tablet according to claim 1, characterised in that the bioadhesive layer contains, in mixture with the bioadhesive material, at least one swelling agent which is insoluble or a swelling agent which is sparingly soluble in the presence of biological fluid, and/or a swelling agent which is soluble or a gelling agent which is soluble in the presence of biological fluid, and, optionally at least one excipient which improves the bioadhesion and/or an auxiliary which is soluble in water or acts as an agent with a hydrophilic nature.

4. Process for the production of bioadhesive tablets, wherein said bioadhesive tablets are produced in the form of multilayers, and wherein at least one bioadhesive layer which, in operation, adheres to a biological tissue or a mucous membrane by impregnation with water or with the biological fluid present in the environment of the tissue or mucous membrane, and which permits the release, as desired, of active principle, is formed by direct compression of a mixture of ingredients which contains the total charge of a bioadhesive material that is essentially composed of a product selected from the group consisting of polymers modified by maleic anhydride and pharmaceutically acceptable derivatives thereof, and at least one active principle layer is formed from a mixture of ingredients containing the majority of the total charge of active principle, and optionally at least one layer is formed from a mixture of ingredients so as to form a barrier to diffusion of active principle and to the penetration of water or of said biological fluid.

5. The tablet according to claim 1, characterised in that the bioadhesive material is essentially composed of a copolymer of methylvinylether and maleic anhydride.

6. The tablet according to claim 3, characterised in that the bioadhesive layer contains 5 to 100% of bioadhesive material, 0 to 80% of insoluble swelling agent or sparingly soluble swelling agent, 0 to 50% of soluble swelling agent or soluble gelling agent, 0 to 50% of excipient which, used in association with the bioadhesive material, may improve bioadhesion, and 0 to 80% of auxiliary which is soluble in water acting as an agent with a hydrophilic nature.

7. The tablet according to claim 1, characterised in that the main layer contains, in mixture with the active principle (s), at least one swelling agent which is insoluble or a swelling agent which is sparingly soluble in the presence of biological fluid, and/or at least one swelling agent which is soluble or a gelling agent which is soluble in the presence of biological fluid with, optionally, at least one excipient which makes it possible to obtain inclusions of active principle and/or at least one excipient which is soluble in water or acts as an agent with a hydrophilic nature, or least one excipient which is insoluble in water or acts as an agent with a hydrophobic nature.

8. The tablet according to claim 7, characterised in that the main layer contains advantageously 70 to 100% of the total charge of active principle of the tablet, 0 to 50% of insoluble swelling agent or sparingly soluble swelling agent, 0 to 50% of soluble swelling agent or soluble gelling agent, 0 to 50% of excipient which makes it possible to obtain inclusions of active principle, 0 to 50% of auxiliary which is soluble in water acting as an agent with a hydrophilic nature, 0 to 50% of auxiliary which is insoluble in water acting as an agent with a hydrophobic nature.

9. The tablet according to claim 2, characterised in that the barrier layer is essentially formed from the active principle in a proportion which may range from 0 to 30% of the total charge, at least one swelling agent which is insoluble or a swelling agent which is sparingly soluble in the presence of biological fluid and/or a swelling agent which is soluble or a gelling agent which is soluble in the presence of biological fluid with, optionally, at least one excipient which makes it possible to obtain inclusions of active principle, and/or an auxiliary which is soluble in water or acts as an agent with a hydrophilic nature and/or at least one agent which is insoluble in water or acts as an agent with a hydrophobic nature.

10. The tablet according to claim 9, characterised in that the barrier layer contains advantageously 0 to 30% of the total charge of active principle of the tablet, 0 to 80% of insoluble swelling agent or sparingly soluble swelling agent, 0 to 80% of soluble swelling agent or soluble gelling agent, 0 to 50% of excipient which makes it possible to obtain inclusions of active principle, 0 to 25% of auxiliary which is soluble in water acting as an agent with a hydrophilic nature, 0 to 50% of auxiliary which is insoluble in water acting as an agent with a hydrophobic nature.

11. A bioadhesive tablet obtained by the process according to claim 4.

12. The process of claim 4, wherein said bioadhesive material is essentially composed of a product selected from the group consisting of polymers modified by maleic anhydride and pharmaceutically acceptable derivatives thereof.

13. The tablet according to claim 3, characterised in that the excipients are selected from the group consisting of guar gum, xanthan gum, carob, carrageenates, pectin, a biological or synthetic protein used alone or in association with other proteins of biological or synthetic origin, cyclodextrins or derivatives, partially methylated betacyclodextrins, and derivatives of acrylic acid.

14. The process of claim 4, wherein said bioadhesive material is essentially composed of a copolymer of methylvinylether and maleic anhydride.

15. The process of claim 4, wherein the mixture of ingredients used for the formation of the bioadhesive layer essentially contains 5 to 100% of bioadhesive material, 0 to 80% of insoluble swelling agent or sparingly soluble swelling agent, 0 to 50% of soluble swelling agent or soluble gelling agent, 0 to 50% of excipient which, used in association with the bioadhesive material, may improve bioadhesion, and 0 to 80% of auxiliary which is soluble in water acting as an agent with a hydrophilic nature.

16. The tablet according to claim 1, in the form of a three-layer tablet, produced for a use by an essentially transmucosal route, in which the internal layer of active principle is covered on its two opposite faces respectively by the bioadhesive layer and the barrier layer, and on the sides either by the bioadhesive layer or by the barrier layer, or it is covered on both its faces by the bioadhesive layer and on its sides by the barrier layer.

17. The tablet according to claim 1, produced for a use by an essentially non-transmucosal route, and formed successively from an external bioadhesive layer, a barrier layer, a layer of active principle, said layers being superposed, or the layer of active principle being, if need be, covered on at least one of the sides by the barrier layer, or the layer active principle being covered on its face with an external barrier layer.

18. The tablet according to claim 1, produced for use by mixed routes, transmucosal or non-transmucosal, and comprise at least one bioadhesive layer, a layer with the active principle and a barrier layer, these layers being superposed, either the barrier layer on one or both sides of the layer of active principle or both external opposite bioadhesive layers with an internal barrier layer and an internal layer of active principle.

19. The process of claim 4, wherein the mixture of ingredients used for the formation of the active principle layer essentially contains 70 to 100% of the total charge of active principle of the tablet, 0 to 50% of insoluble swelling agent or sparingly soluble swelling agent, 0 to 50% of soluble swelling agent or soluble gelling agent, 0 to 50% of excipient which makes it possible to obtain inclusions of active principle, 0 to 50% of auxiliary which is soluble in water acting as an agent with a hydrophilic nature, 0 to 50% of auxiliary which is insoluble in water acting as an agent with a hydrophobic nature.

20. The tablet according to claim 1, characterised in that it contains coated or uncoated minigranules, microcapsules, nanoparticles or nanocapsules.

21. The process of claim 4, wherein the mixture of ingredients used for the formation of the barrier layer essentially contains 0 to 30% of the total charge of active principle of the tablet, 0 to 80% of insoluble swelling agent or sparingly soluble swelling agent, 0 to 80% of soluble swelling agent or soluble gelling agent, 0 to 50% of excipient which makes it possible to obtain inclusions of active principle, 0 to 25% of auxiliary which is soluble in water acting as an agent with a hydrophilic nature, 0 to 50% of auxiliary which is insoluble in water acting as an agent with a hydrophobic nature.

22. The application of the tablet according to claim 1, in man and animals, wherein said application is selected from the group consisting of a medical application, a therapeutic application, a preventive application, and a health application.

23. The tablet according to claim 1, wherein said pharmaceutically acceptable derivatives are selected from the group consisting of the pharmaceutically acceptable acid, esters and salts of polymers modified by maleic anhydride.

* * * * *